United States Patent
Zhou

(10) Patent No.: US 10,145,817 B2
(45) Date of Patent: Dec. 4, 2018

(54) ANTI-TRADITIONAL VERTICAL SLICE GEL ELECTROPHORESIS CELL AND A TELESCOPIC URGING MECHANISM

(71) Applicant: Deming Zhou, Allen, TX (US)

(72) Inventor: Deming Zhou, Allen, TX (US)

( * ) Notice: Subject to any disclaimer, the term of this patent is extended or adjusted under 35 U.S.C. 154(b) by 0 days.

(21) Appl. No.: 14/757,285

(22) Filed: Dec. 11, 2015

(65) Prior Publication Data
US 2016/0334368 A1 Nov. 17, 2016

Related U.S. Application Data

(60) Provisional application No. 62/124,463, filed on Dec. 19, 2014.

(51) Int. Cl.
*G01N 27/453* (2006.01)
*G01N 27/447* (2006.01)

(52) U.S. Cl.
CPC ..... *G01N 27/44704* (2013.01); *G01N 27/453* (2013.01)

(58) Field of Classification Search
CPC .............. G01N 27/44756; G01N 27/453
See application file for complete search history.

(56) References Cited

U.S. PATENT DOCUMENTS 8,808,520 B2 * 8/2014 Zhou ................ B01D 57/02
204/618

OTHER PUBLICATIONS

Oxford English Dictionary definition of "ark" downloaded from https://en.oxforddictionaries.com/definition/ark on Sep. 21, 2016, 3 pages.*

* cited by examiner

*Primary Examiner* — Alexander S Noguerola

(57) ABSTRACT

Vertically cut a "quasi-upper buffer chamber" (such as the part 11 of US 8808520) into 2 pieces of U-shaped door-frames, and then fix them onto the 2 opposite side walls of a transparent ark, so as to divide the ark into 3 compartments. Position a tubular telescopic urging mechanism into the middle compartment, and then use it to push 2 vertical slice gel cassettes to resting against the 2 door-frames respectively, so as to convert the 3 compartments into 3 watertight compartments. Wherein, the middle one is the lower buffer chamber, while the other 2 are the 2 upper buffer chambers of the present anti-traditional vertical slice gel electrophoresis cell.

4 Claims, 4 Drawing Sheets

ANTI-TRADITIONAL VERTICAL SLICE GEL ELECTROPHORESIS CELL AND A TELESCOPIC URGING MECHANISM

REFERENCED TO RELATED APPLICATIONS

This application clams the benefit of provisional application 62/124,463 filed on Dec. 19, 2014 to USPTO

FIELD OF THE INVENTION

This invention relates to the design of vertical slice gel electrophoresis device and specifically to the design of anti-traditional vertical slice gel electrophoresis cell and a telescopic urging mechanism.

PRIOR ART AND THE COMMENT

Vertical slice gel electrophoresis is a kind of electrophoresis technique mainly used for protein separation, wherein the electrophoresis takes place in slice shaped gel media hold in vertical gel cassette. After the electrophoresis is finished, allow the cassette to be prized open, and take the gel slice off for the following analysis. In the electrophoresis apparatus, a container that is in communication with the upper opening of the gel cassette is called the upper buffer chamber (UBC); and the wherein electrode is an upper electrode. The lower buffer chamber (LBC), and the lower electrode are defined by the same way.

The key point of design a vertical slice gel electrophoresis cell is how to make the upper opening of the vertical slice gel cassette in communication with the UBC without leakage? The solution in the prior art was that: firstly to make one sidewall of each vertical slice gel cassette to have a U-notched upper opening (refer to the FIG. 3 of U.S. Pat. No. 4,560,459, please); and then use an urging mechanism to force 2 pieces of such kind vertical slice gel cassettes to sandwich a U-shaped quasi-UBC (refer to the part 11 of U.S. Pat. No. 8,808,520; the part 14 of U.S. Pat. No. 4,560,459; or the part 53 of U.S. Pat. No. 6,001,233, please) tightly in between of them. Thereupon, a UBC/cassette complex is formed, and the both U-notched upper openings of the 2 gel cassettes are exposed to the inside of the complex simultaneously. Afterwards, as long as to place the UBC/cassette complex down into a LBC, thereupon a traditional vertical slice gel electrophoresis cell is formed. Wherein, the U.S. Pat. No. 4,563,459 and U.S. Pat. No. 6, 001,233 both use a cam-lever as the urging mechanism for forcing 2 gel cassettes to sandwich the UBC in between of them. But, in U.S. Pat. No. 8,808,520, a larger diameter screw urging ring is employed as the urging mechanism. Thereby additionally making the electrophoresis cell has some compatibility to deal with those thicknesses different gel cassettes from the market.

SUMMARY OF THE INVENTION

The present invention is developed out by getting enlightenment from U.S. Pat. No. 8,808,520. The idea is: on one hand, to vertical cut a quasi-UBC (such as the part 11 of U.S. Pat. No. 8,808,520) into 2 pieces of U-shaped doorframes, and then to fix them onto the 2 opposite sidewalls of a transparent ark respectively. The existing of the 2 U-shaped doorframes has already divided the ark into 3 compartments. On the other hand, to convert a turnbuckle into a plastic tubular telescopic urging mechanism, and then place it into the middle compartment, using it to push 2 pieces of vertical slice gel cassettes to let them to rest against the 2 doorframes respectively. As the result, converts the 3 compartments into 3 watertight compartments. Among them, the middle one is the LBC, while the other 2 are the 2 UBCs of the present anti-traditional vertical slice gel electrophoresis cell. Anti-traditional styled electrophoresis cell has only 2 components, the 2 gel cassettes have been moved to the 2 sides and their upper openings been turned to face to the 2 sides of the cell. All of these arrangements are favorable for the sample loading as well as for the electrophoresis monitoring. In addition, the center located urging mechanism can no longer block up the visual line of the operator; plus the employed screwing urging mechanism can additionally bring about a compatibility to enable the electrophoresis cell to deal with those thicknesses different gel cassettes from the market.

DETAILED DESCRIPTION OF THE PREFERRED EMBODIMENTS

Figure 1:
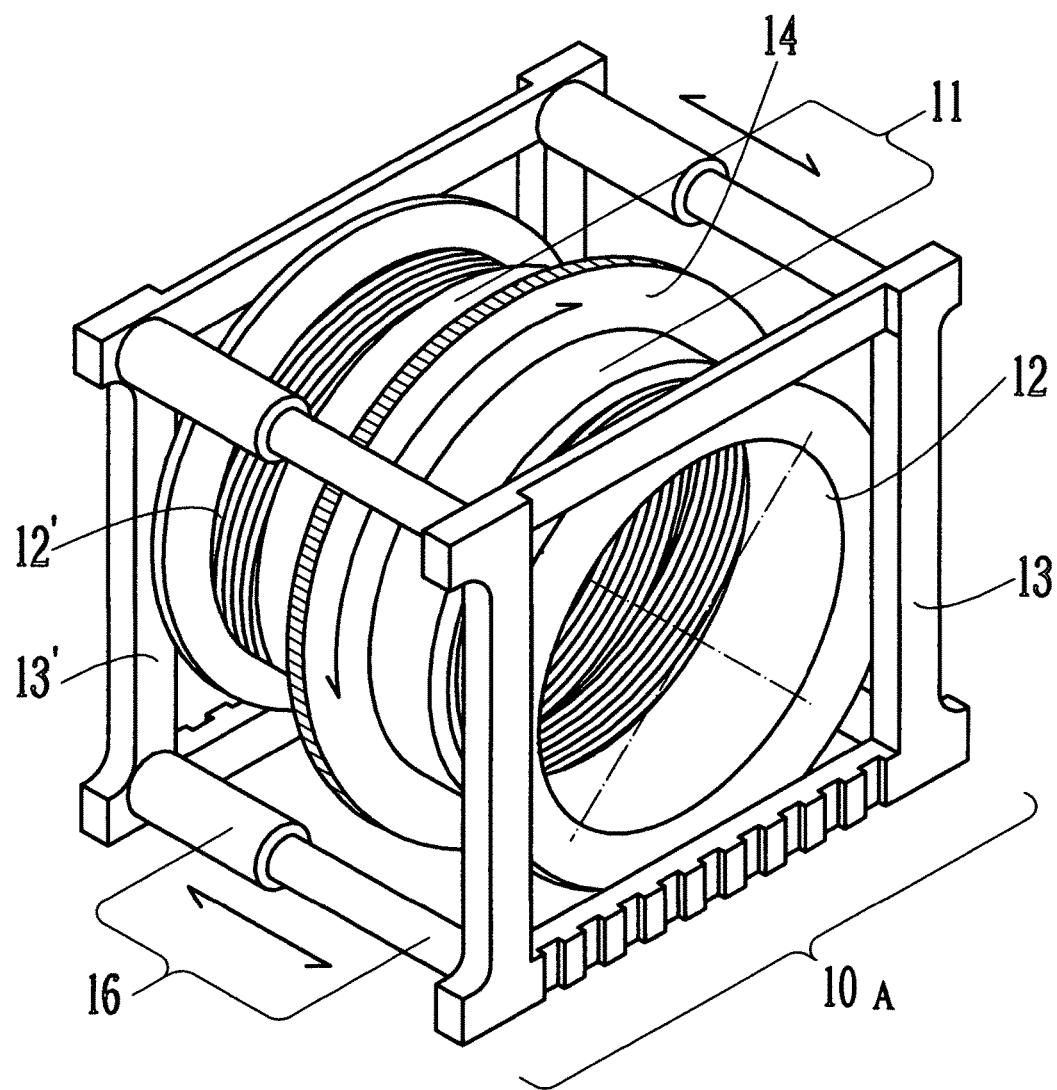
FIG. 1 is a perspective view of the tubular telescopic urging mechanism 10A that is the critical component of the present anti-traditional vertical slice gel electrophoresis cell.

FIG. 1 is a perspective view of the telescopic screwing urging mechanism 10A that is the critical component of the present anti-traditional vertical slice gel electrophoresis cell, is made of plastic having a tubular telescopic structure. Wherein, the center rotatable sleeve 11 uses its one end to be rotatable coupled with the threaded tube 12 by forehand thread, while uses its other end to be rotatable coupled with the other threaded tube 12' by backhand thread. Therefore, turning the sleeve 11 in different directions can cause the 2 side threaded tubes 12 and 12', as well as the 2 frames 13 and 13', to move away from each other or to retraction back. The flange disk 14 is for facilitate people to easy rotate the sleeve 11. The function of the 4 pairs of telescopic fishing poles 16$s$ is for holding the two end frames 13 and 13' always in a same vector. This telescopic urging mechanism 10A has the same working principle as that of the turnbuckles. But this one is intend to use in the present anti-traditional slice gel electrophoresis cell for pushing 2 pieces of the engaged vertical slice gel cassettes to join the 2 UBCs separately and simultaneously. Frames 13 and 13' are used for transmitting and distributing the pressures to the engaged vertical slice gel cassettes. This kind telescopic screwing urging mechanism as 10A can be simplified to let its 1 side coupling without thread involved in the coupling. But the simplified structure is still covered under the present idea.

Figure 2:
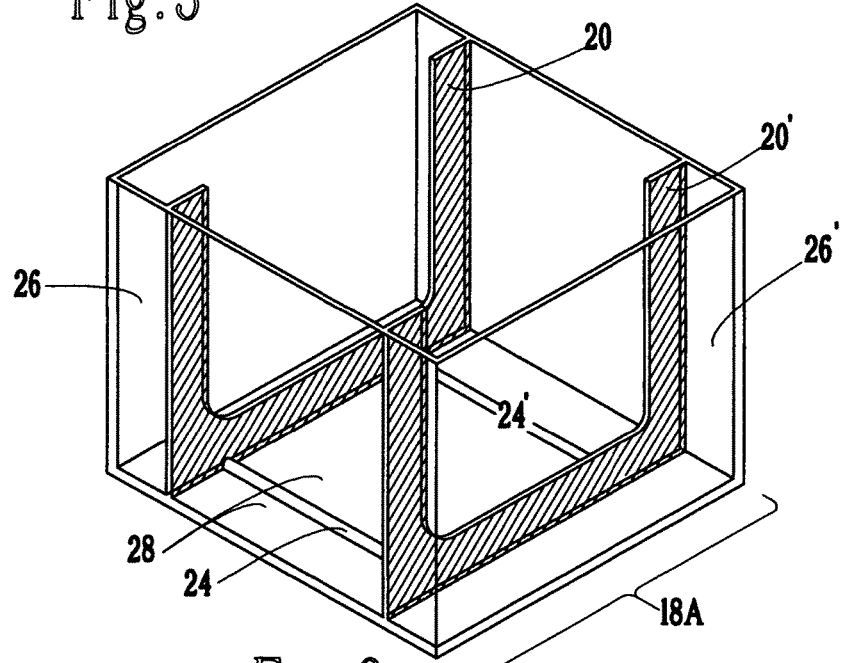
FIG. 2 is a perspective view of a transparent ark that is the main body of the present anti-traditional vertical slice gel electrophoresis cell. Wherein, the 2 parallel doorframes are emphasized there by marking them with section lines.

FIG. 2 is a perspective view of a transparent ark 18A that is the main body of the present anti-traditional vertical slice gel electrophoresis cell. It is a container made of transparent material, has a profile size that is slightly larger than the engaged vertical slice gel cassettes. Wherein, the pair of U-shaped doorframes 20 and 20' (have been emphasized there, by marking them with section marking lines) are paralleled to each other, and also be face to face to each other. Both U-shaped doorframes use their U-shaped outer-edges to fix on the opposite 2 side walls, as well as on the bottom plate of the transparent ark 18A. However, in the other situation, as described in the abstract and the summary 2 chapters, wherein the 2 U-shaped doorframes use their U-shaped reverse sides to fix onto the opposite 2 side walls respectively of the transparent ark 18A and then let their 2 U-shaped front sides to face to each other. However, if 2 object in face to face relationship, they are also in parallel relationship. Anyway in the both situations, the existing of the 2 doorframes have already divided the ark 18A into a left 26, a middle 28 and a right 26' three compartments. The 24 and 24' are 2 convex ribs, functionally to elevate the engaged gel cassettes to a little higher position from the bottom of the ark 18A.

Figure 3:
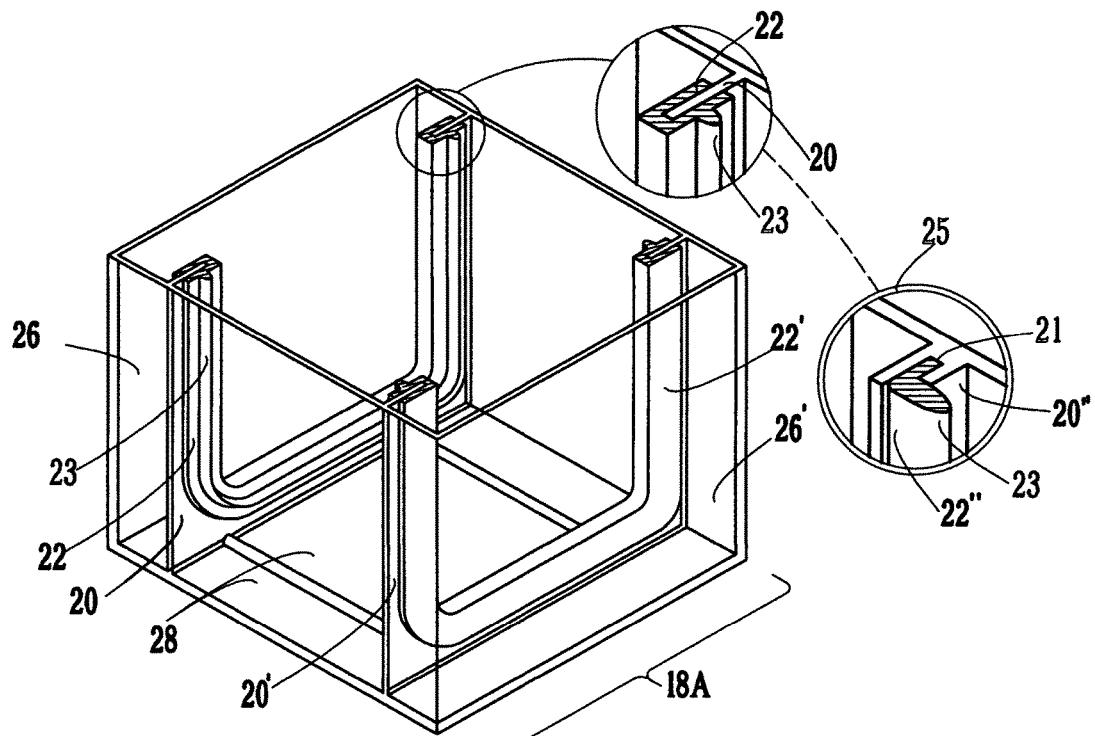
FIG. 3 is another perspective view of the transparent ark after the 2 U-shaped rubber sealing gaskets have affixed on the 2 U-shaped doorframes respectively.

FIG. 3 is another perspective view of the transparent ark 18A as shown in FIG. 2. Wherein, the 2 U-shaped rubber sealing gasket 22 and 22' have already affixed along the 2 U-shaped doorframes 20 and 20' respectively, and each sealing gasket 22 and 22' with its U-shaped flange 23 or 23' to point to the other doorframe, as shown in the FIG. 3. In addition, it had batter to make the U-shaped doorframe 20 and 20' to be more thicker as the doorframe 20" as showing in the double circles 25, and then to dig a groove 21 along the U-shaped thicker doorframe 20", so as to enable the groove 21 to hold the edge-fold of the U-shaped rubber sealing gasket 22", but still let its U-shaped flange 23 to point to the other U-shaped doorframe.

Figure 4:
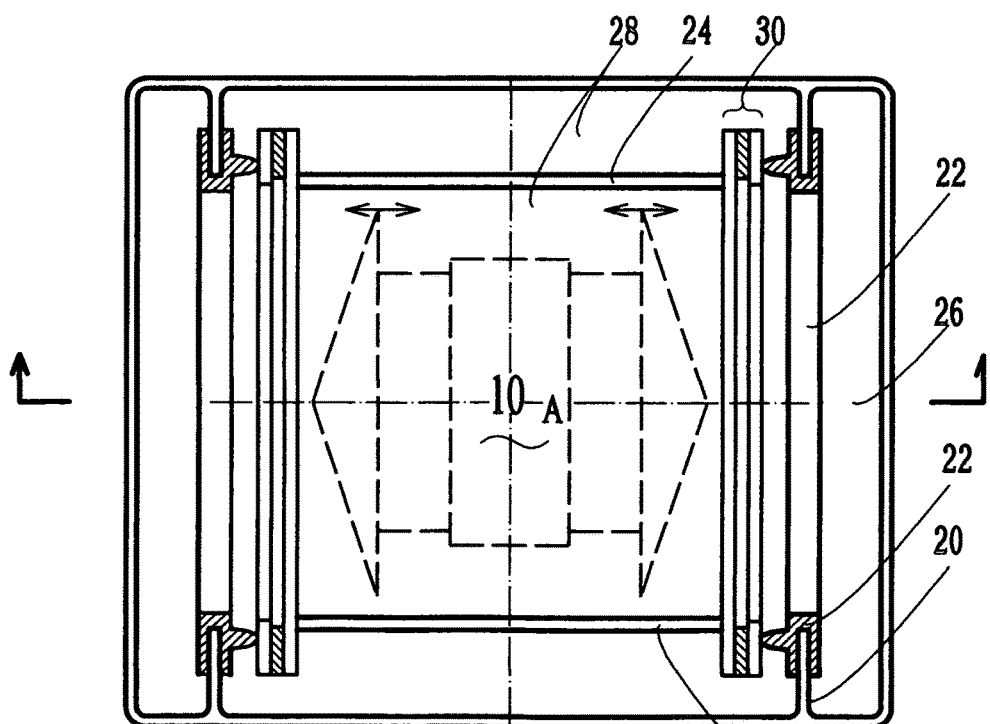
FIG. 4 is the tope view of FIG. 3, but already have 2 vertical slice gel cassettes 10 and 10' and the telescopic urging mechanism 10A been placed in their positions respectively.

FIG. 4 is the tope view of FIG. 3. Wherein, the 2 engaged vertical slice gel cassettes 30, 30', and the telescopic urging mechanism 10A have been placed in their positions respectively. But, the telescopic urging mechanism 10A is represented by its cartoon drawing. Besides, some of other characteristic-less parts, such as the upper and low electrode wires and the banana plugs have been omitted from this FIG. 4. (However, the principle of layout the electrodes is still same as that as in the traditional electrophoresis cell that is let a length of bareness platinum wire to be arranged to parallel to the openings of the gel cassettes, and let it to connect to a banana plug mounted atop the apparatus via a length of covered platinum wire between them).

Figure 5:
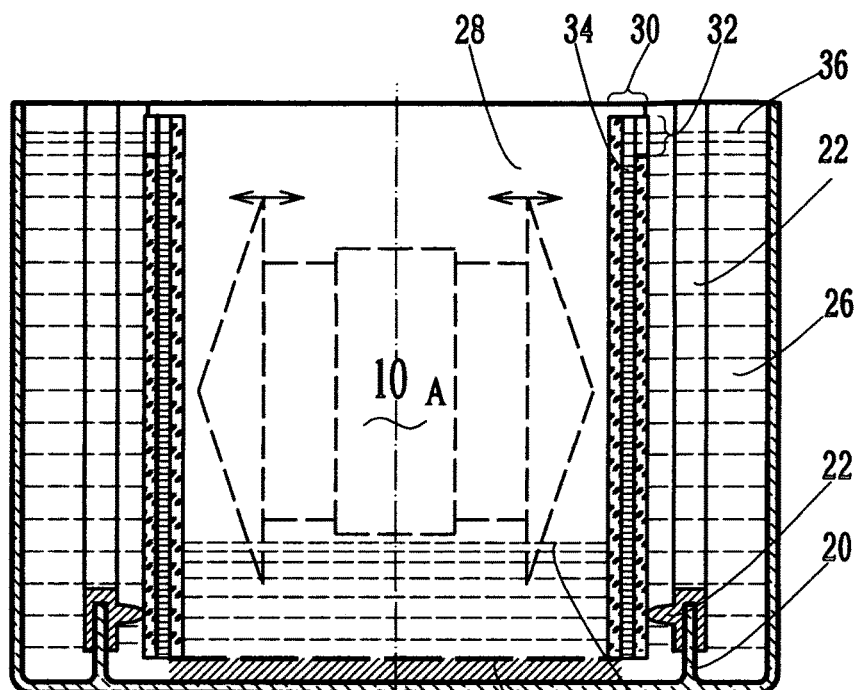
FIG. 5 is the longitudinal sectional view of FIG. 4, wherein additionally expressed the existence of the upper and lower buffer solutions.

FIG. 5 is the longitudinal sectional view of FIG. 4. Wherein, the telescopic urging mechanism 10A has pushed the 2 gel cassettes 30 and 30' to rest against the 2 U-shaped sealing gaskets 22 and 22' respectively. As a result, the hereby formed two water tight compartments 26 and 26' become the 2 UBCs, and the middle water compartment 28 become the LBC of the present anti-traditional vertical slice electrophoresis cell. This FIG. 5 is also expressed the existence of the upper and lower buffer solutions; the altitudes 36 and 38 are the upper and lower buffer solution should to arrived at respectively; and how the upper buffer solution 36 can contact the upper end 34 of the gel slice by crossing the U-notched upper opening 32 of the gel cassette 30, etc. The thick dash-line 24 representatives the 2 convex ribs 24 and 24' as showed in FIG. 2, functionally for uplift the bottom openings of the cassettes 30 and 30'.

Figure 6:
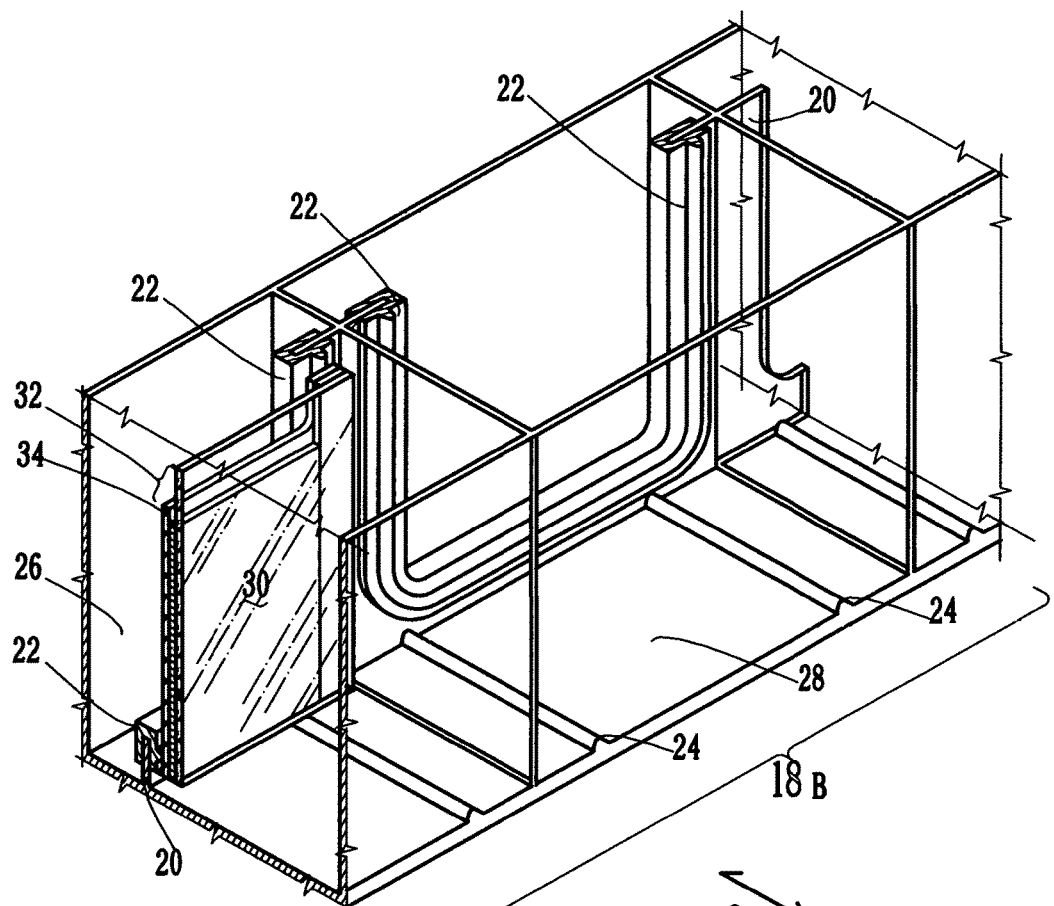
FIG. 6 is a broken perspective view of a multi-compartment transparent ark 18B.

FIG. 6 is a broken perspective view of the multi-compartment transparent ark 18B. Wherein a length of the U-shaped doorframe 20 is presented there in the right compartment; a U-shaped rubber sealing gasket 22 is there affixed onto the doorframe 20 in the middle compartment; and a vertical slice gel cassette 30 is there in its position within the left compartment.

Figure 7:
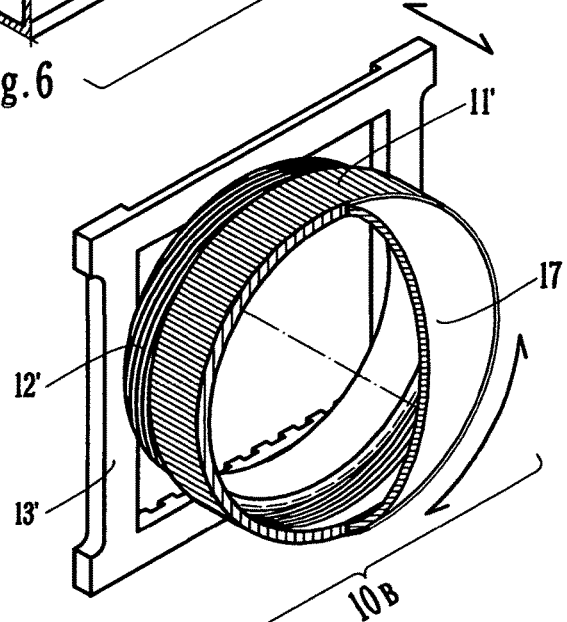
FIG. 7 is a broken perspective view of a simplified telescopic screwing urging mechanism 10B that has only one pushing frame.

FIG. 7 is a broken perspective view of the simplified telescopic urging mechanism 10B that has only one pushing frame 13'at the one end. Wherein, the rotatable sleeve 11' has a dome end 17, but uses the other end to be rotatable coupled on the threaded tube 12', which has a pushing frame 13' at the other end. Turning the rotatable sleeve 11' can make the pushing frame 13' to push one vertical slice gel cassette to rest against the U-shaped rubber sealing gasket 22 by letting the dome end 17 to rest against a side wall of a transparent ark.

What is claimed is:

1. A non-traditional vertical slice gel electrophoresis cell having an urging mechanism, wherein said electrophoresis cell has a main body that is a box-shaped container, made of transparent plastic having at least one pair of U-shaped frames fixed at the inside thereof; each of said U-shaped frame has a U-shaped rubber sealing gasket rimmed along it when there is one pair of said U-shaped frames fixed at the inside of the box-shaped container, the pair of said U-shaped frames divide the inside of the box-shaped container into three compartments, which are two side compartments and one middle compartment; the middle compartment is for housing said urging mechanism as well as two vertical slice gel cassettes; when the two vertical slice gel cassettes are pushed to rest against said two U-shaped rubber sealing gaskets respectively, resulted in the three compartments become three water-tight compartments, wherein the two side water-tight compartments are the two upper buffer chambers of the present electrophoresis cell, while the middle water-tight compartment is the lower buffer chamber thereof.

2. A non traditional vertical slice gel electrophoresis cell having an urging mechanism, wherein said urging mechanism is made of plastic comprising one center threaded tube and two aside threaded tubes; one end of said center threaded tube is rotatably coupled with one of said two aside threaded tube by screwing the left-handed thread of one tube onto the left-handed thread of the other tube; while the other end of said center threaded tube is rotatably coupled with the other of said two aside threaded tubes by screwing the right-handed thread of one tube onto the right-handed thread of the other tube; each of said aside threaded tube has a square frame at the un-coupled end mainly for pushing against a vertical slice gel cassette; turning said center threaded tube in one direction will cause said urging mechanism to stretch axially, while turning said center threaded tube in the opposite direction will cause said urging mechanism to shorten axially.

3. The non-traditional vertical slice gel electrophoresis cell of claim 2, wherein said urging mechanism further comprises a flanged ring at the middle of said center threaded tube for turning it more easily, and also comprises four pairs of retractable tubules connected with the corresponding corners of said two square frames, functionally for preventing said urging mechanism from twisting.

4. A non-traditional vertical slice gel electrophoresis cell having an urging mechanism, wherein said urging mechanism is made of plastic comprising one rotatable threaded tube and one non-rotatable threaded tube; the two threaded tubes are rotatably coupled to each other by screwing one thread tube onto the other thread tube; said rotatable threaded tube has a convex closed un-coupled end, while said non-rotatable threaded tube has a square frame at the un-coupled end for pushing against a vertical slice gel cassette as well as for preventing the tube from rotation; turning said rotatable threaded tube in one direction will cause said urging mechanism to stretch axially, while turning said rotatable threaded tube in the opposite direction will cause said urging mechanism to shorten axially.

* * * * *